United States Patent [19]

Heymanns et al.

[11] Patent Number: 5,403,954
[45] Date of Patent: Apr. 4, 1995

[54] PREPARATION OF METHYLTRIS(M-SULFONATOPHENYL) PHOSPHONIUM IODIDE TRISODIUM SALT AND USE THEREOF IN CARBONYLATION REACTIONS TO PREPARE CARBOXYLIC ACIDS AND/OR THEIR ESTERS

[75] Inventors: Peter Heymanns, Essen; Erhard Jägers, Bornheim; Andreas Seidel, Köln; Hermann Berwe, Hürth, all of Germany

[73] Assignee: Hoechst Aktiengesellschaft, Frankfurt am Main, Germany

[21] Appl. No.: 177,909

[22] Filed: Jan. 6, 1994

[30] Foreign Application Priority Data

Jan. 20, 1993 [DE] Germany .................. 43 01 310.4

[51] Int. Cl.$^6$ .......................... C07C 51/12; C07F 9/54
[52] U.S. Cl. ..................................... 562/519; 562/522
[58] Field of Search ............................ 562/519, 522

[56] References Cited

U.S. PATENT DOCUMENTS

| | | | |
|---|---|---|---|
| 4,483,804 | 11/1984 | Rizkalla | 562/891 |
| 4,536,354 | 8/1985 | Drent | 562/891 |
| 4,625,058 | 11/1986 | Fujiwa et al. | 562/519 |
| 5,026,907 | 6/1991 | Wegman et al. | 562/519 |
| 5,214,203 | 5/1993 | Koyama et al. | 562/519 |

Primary Examiner—Arthur C. Prescott
Attorney, Agent, or Firm—Connolly & Hutz

[57] ABSTRACT

In a process for preparing methyltris(m-sulfonatophenyl)phosphonium iodide trisodium salt, the sodium salt of trisulfonated triphenylphosphine and methanol are introduced as the initial charge, a solution of methyl iodide in methanol is added dropwise at elevated temperature, and after an additional reaction time the reaction product is evaporated to dryness in vacuo.

Methyltris(m-sulfonatophenyl)phosphonium iodide trisodium salt can be used to prepare carboxylic acids and/or their esters by carbonylation of saturated aliphatic alcohols having from 1 to 20 carbon atoms or their halo, ester or ether derivatives over a rhodium catalyst in the presence of water and methyl iodide under a CO partial pressure of from 0.3 to 200 bar at a temperature of from 100° to 240° C., provided methyltris(m-sulfonatophenyl)phosphonium iodide trisodium salt and carboxylic acid are added to the liquid phase prior to carbonylation.

13 Claims, No Drawings

PREPARATION OF METHYLTRIS(M-SULFONATOPHENYL) PHOSPHONIUM IODIDE TRISODIUM SALT AND USE THEREOF IN CARBONYLATION REACTIONS TO PREPARE CARBOXYLIC ACIDS AND/OR THEIR ESTERS

The invention relates to a process for preparing methyltris (m-sulfonatophenyl)phosphonium iodide trisodium salt and to the use thereof in carbonylation reactions to prepare carboxylic acids and/or their esters.

Starting from the sodium salt of trisulfonated triphenylphosphine, a technically simple process for preparing methyltris(m-sulfonatophenyl)phosphonium iodide trisodium salt $[CH_3-P^{\oplus}(C_6H_4SO_3Na)_3I^{\ominus}]$ has been found. The compound prepared is a pale yellowish crystalline solid. The phosphorus content determined by analysis is 3.93% by weight; the solubility in water is 1420 g/kg at 20° C., corresponding to a 58% by weight strength saturated solution. $^{31}$P-NMR: $Me-P^+(C_{ph})_3 = 26.05$ ppm in $D_2O$/acetone-$d_6$.

The process of the invention comprises introducing the sodium salt of trisulfonated triphenylphosphine and methanol as the initial charge, adding a solution of methyl iodide in methanol dropwise at elevated temperature, and after an additional reaction time evaporating the reaction product to dryness in vacuo, preferably at from 25 to 80° C.

In further preferred and alternative embodiments of the process,
a) stoichiometric amounts of the sodium salt of trisulfonated triphenylphosphine are reacted with methyl iodide,
b) the sodium salt of trisulfonated triphenylphosphine is used in the form of a from 20 to 30% by weight strength aqueous solution;
c) the reaction temperature is maintained at from about 30° to 40° C.;
d) the additional reaction time is from 0.5 to 5 hours;
e) the reaction product is evaporated to dryness in a water-pump vacuum. U.S. Pat. No. 5,214,203 describes a process for preparing acetic acid by liquid phase carbonylation, in which methanol or methyl acetate is reacted with CO in the presence of a catalyst system containing rhodium components and an alkyl iodide or bromide. The catalyst system can additionally contain onium-type iodides of phosphorus. U.S. Pat. No. 5,026 907 describes a process for preparing carboxylic anhydrides using specific organic phosphorus compounds and rhodium as the catalyst system.

The phosphorus compounds used as cocatalyst have the disadvantage that catalyst components precipitate in the liquid phase, which makes a continuous carbonylation reaction difficult because of sedimentation and leads to a reduced space-time yield because of the lowered concentration of catalyst components in the liquid phase. U.S. Pat. No. 4,625,058 discloses a process whereby attempts were made to prevent the precipitation of the catalyst components by additions of boron, bismuth and tertiary amide compounds. The additives described therein do not prevent the precipitation of catalyst components in the presence of phosphorus compounds.

It has now been surprisingly found that no precipitation of catalyst components occurs if, in a process for preparing carboxylic acids and/or their esters by carbonylation of saturated aliphatic alcohols having from 1 to 20 carbon atoms or their halo, ester or ether derivatives with a rhodium catalyst in the presence of water and methyl iodide under a CO partial pressure of from 0.3 to 200 bar at a temperature of from 100° to 240° C., methyltris(m-sulfonatophenyl)phosphonium iodide trisodium salt and carboxylic acid are added to the liquid phase prior to carbonylation.

In further preferred and alternative embodiments of the process of the invention for preparing carboxylic acids and/or their esters by carbonylation,
f) the liquid phase prior to the carbonylation reaction contains from 10 to 250 g/kg of methyltris(m-sulfonatophenyl) phosphonium iodide trisodium salt;
g) the liquid phase prior to the carbonylation reaction contains from 250 to 750 g/kg of acetic acid as the carboxylic acid;
h) the liquid phase prior to the carbonylation reaction contains from $10^-$ to 2 mol/l of methyltris(m-sulfonatophenyl) phosphonium iodide trisodium salt, from 3 to 13 mol/l of acetic acid, from $10^{-4}$ to $2 \times 10^{-2}$ mol/l of rhodium, from $10^{-2}$ to 2 mol/l of methyl iodide, from 1 to 20 mol/l of water and from 1 to 5 mol/l of methanol;
i) part of the methyl iodide is replaced by bromine, iodine or a compound of these halogens;
j) up to 50mol% of the methyl iodide is replaced by compounds of Li, Na, K, Mg, Ca, Ba or by tetraalkylammonium salts having from 1 to 20 carbon atoms in each carbon chain;
k) iodides are used as the compounds of Li, Na, K, Mg, Ca, Ba or as the tetraalkylammonium salts.

Particularly suitable iodine compounds are the iodides of lithium, sodium, potassium or ammonium, or hydrogen iodide.

The invention is more particularly described by the Examples.

EXAMPLE 1

Preparation of methyltris(m-sulfonatophenyl)phosphonium iodide trisodium salt 892 g of trisulfonated triphenylphosphine sodium salt (32% by weight strength aqueous solution corresponding to 0.5 mol) were mixed with 800 ml of methanol, and a solution of 71 g of methyl iodide (0.5 mol) in 100 ml of methanol was added dropwise over 30 minutes at 35° C. The mixture was allowed to react for an additional 2 hours. The reaction solution was evaporated to dryness in a rotary evaporator at 40°–50° C. under a water-pump vacuum. 356 g of $[CH_3-P^{\oplus}(C_6H_4SO_3Na)_3 I^{\ominus}]$ were obtained.

EXAMPLE 2

Carbonylation of methanol 1.11 g of rhodium acetate (5 mmol), 71.3 g of methyltris (m-sulfonatophenyl)phosphonium iodide trisodium salt (0.1 mol), 350 g of acetic acid (5.83 mol), 40 g of methanol (1.25 mol) and 50 g of water (2.78 mol) were mixed in a 1 l stirred autoclave at room temperature, and 71 g of methyl iodide (0.5 mol) were subsequently added. After flushing the gas atmosphere with carbon monoxide a number of times, this solution was heated to 140° C. An initial pressure of 5 bar was obtained. After pressurizing with carbon monoxide to a total pressure of 14 bar, constant pressure was reached within 85 minutes. The selectivity to acetic acid was 98.5% with a space-time yield of 1.8 mol/l h. The reddish-brown solution of product contained no precipitates. No leftover methanol was detected by gas chromatography. The methyl acetate content was 0.2% by weight, corresponding to a selectivity of 1.5% based on the methanol used.

We claim:

1. A process for preparing methyltris(m-sulfonatophenyl)phosphonium iodide trisodium salt, which comprises introducing the sodium salt of trisulfonated triphenylphosphine and methanol as the initial charge, adding a solution of methyl iodide in methanol dropwise at elevated temperature, and after an additional reaction time evaporating the reaction product to dryness in vacuo.

2. The process as claimed in claim 1, wherein stoichiometric amounts of the sodium salt of trisulfonated triphenylphosphine are reacted with methyl iodide.

3. The process as claimed in claim 1, wherein the sodium salt of trisulfonated triphenylphosphine is used in the form of a from 20 to 30% by weight strength aqueous solution.

4. The process as claimed in claim 1, wherein the reaction temperature is maintained at from 30° to 40° C.

5. The process as claimed in claim 1, wherein the additional reaction time is from 0.5 to 5 hours.

6. The process as claimed in claim 1, wherein the reaction product is evaporated to dryness in a water-pump vacuum.

7. A process for preparing at least one substance selected from carboxylic acids and their esters by carbonylation of saturated aliphatic alcohols having from 1 to 20 carbon atoms or their halo, ester or ether derivatives over a rhodium catalyst in the presence of water and methyl iodide under a CO partial pressure of from 0.3 to 200 bar at a temperature of from 100° to 240° C. which comprises adding methyltris(m-sulfonatophenyl)phosphonium iodide trisodium salt and carboxylic acid to the liquid phase prior to carbonylation.

8. The process as claimed in claim 7, wherein the liquid phase prior to the carbonylation reaction comprises from 10 to 250 g/kg of methyltris(m-sulfonatophenyl)phosphonium iodide trisodium salt.

9. The process as claimed in claim 7, wherein the liquid phase prior to the carbonylation reaction comprises from 250 to 750 g/kg of acetic acid as the carboxylic acid.

10. The process as claimed in claim 7, wherein the liquid phase prior to the carbonylation reaction comprises from $10^{-1}$ to 2 mol/l of methyltris(m-sulfonatophenyl)phosphonium iodide trisodium salt, from 3 to 13 mol/l of acetic acid, from $10^{-4}$ to $2\times10^{-2}$ mol/l of rhodium, from $10^{-2}$ to 2 mol/l of methyl iodide, from 1 to 20 mol/l of water and from 1 to 5 mol/l of methanol.

11. The process as claimed in claim 10, wherein part of the methyl iodide is replaced by bromine, iodine or a compound of these halogens.

12. The process as claimed in claim 10, wherein up to 50 mol % of the methyl iodide is replaced by compounds of Li, Na, K, Mg, Ca, Ba or by tetraalkylammonium salts having from 1 to 20 carbon atoms in each carbon chain.

13. The process as claimed in claim 10, wherein iodides are used as the compounds of Li, Na, K, Mg, Ca, Ba or as the tetraalkylammonium salts.

* * * * *